United States Patent [19]

Cannelongo

[11] Patent Number: 5,650,161
[45] Date of Patent: Jul. 22, 1997

[54] SAFENED PESTICIDAL RESIN COMPOSITIONS FOR CONTROLLING SOIL BORNE PESTS AND PROCESS FOR THE PREPARATION THEREOF

[75] Inventor: Joseph Fredrick Cannelongo, Piscataway, N.J.

[73] Assignee: American Cyanamid Company, Madison, N.J.

[21] Appl. No.: 464,190

[22] Filed: Jun. 5, 1995

Related U.S. Application Data

[60] Continuation of Ser. No. 239,850, May 9, 1994, which is a division of Ser. No. 925,326, Aug. 6, 1992, abandoned, which is a continuation of Ser. No. 447,960, Dec. 7, 1989, abandoned, which is a continuation of Ser. No. 114,821, Nov. 5, 1987, abandoned, which is a continuation-in-part of Ser. No. 933,842, Dec. 24, 1986.

[51] Int. Cl.⁶ .................................................. A01N 25/08
[52] U.S. Cl. .......................... 424/405; 424/406; 424/408; 424/409; 424/419; 424/78.31; 574/109
[58] Field of Search .................................. 424/405, 406, 424/408, 409, 419, 78.18, 78.31, 489; 524/489, 423; 574/126, 109, 144

[56] References Cited

U.S. PATENT DOCUMENTS

| | | | |
|---|---|---|---|
| Re. 32,356 | 2/1987 | Cardarelli | 424/78 |
| 3,318,769 | 5/1967 | Folckemer et al. | 514/144 |
| 3,344,021 | 9/1967 | Menn et al. | 514/144 |
| 3,627,707 | 12/1971 | Giessler et al. | 524/423 |
| 3,862,066 | 1/1975 | Reiter et al. | 524/489 |
| 4,041,151 | 8/1977 | Milionis et al. | 424/78 |
| 4,198,782 | 4/1980 | Kydonieus et al. | 47/58 |
| 4,299,841 | 11/1981 | Geering | 424/282 |
| 4,331,678 | 5/1982 | De'Ath et al. | 424/273 |
| 4,343,790 | 8/1982 | Pasarela | 424/81 |
| 4,385,016 | 5/1983 | Gwinn | 264/37 |
| 4,400,374 | 8/1983 | Cardarelli | 424/78 |
| 4,405,360 | 9/1983 | Cardarelli | 71/117 |
| 4,435,383 | 3/1984 | Wysong | 424/78 |
| 4,440,360 | 4/1984 | Carderlli | 71/117 |
| 4,485,103 | 11/1984 | Pasarela | 424/78 |
| 4,554,155 | 11/1985 | Allan et al. | 424/78 |
| 4,657,582 | 4/1987 | Huber | 71/121 |
| 4,674,445 | 6/1987 | Cannelongo | 119/156 |
| 4,810,793 | 3/1989 | Kozuma et al. | 424/78 |

FOREIGN PATENT DOCUMENTS

| | | |
|---|---|---|
| 1099628 | 10/1977 | Canada . |
| 0064379 | 11/1982 | European Pat. Off. . |
| 49-19003 | 4/1973 | Japan . |
| 53-74551 | 12/1977 | Japan . |
| 60-237007 | 5/1984 | Japan . |
| 1425127 | 4/1973 | United Kingdom . |
| 2053685 | 2/1981 | United Kingdom . |

OTHER PUBLICATIONS

Journal of Agricultural and Food Chemistry, vol. 21, No. 1,Jan.–Feb. 1973, pp. 103–108, Washington, DC, US; R.A. Stokes et al.

*Primary Examiner*—Neil S. Levy
*Attorney, Agent, or Firm*—Joseph M. Mazzarese

[57] ABSTRACT

The present invention relates to novel dry-blended extrudable pesticidal resin composition, extruded pesticidal resin compositions and pelletized pesticidal resin compositions comprising, as the active ingredient, O,O-diethyl S-[[1,1-dimethylethyl)thio]methyl]phosphorodithioate, O,O-diethyl S-(ethylthiomethyl)phosphorodithioate or a pesticidal chemical wherein said technical grade of said pesticidal chemical has a dermal and/or oral $LD_{50}$, as measured on rats or rabbits of less than 50 mg/kg. The novel compositions of the present invention are characterized by markedly reduced mammalian toxicity and increased pesticide stability and are essentially free of dust. Further, the present invention also relates to a process for preparing the present safened pesticidal resin compositions.

16 Claims, No Drawings

SAFENED PESTICIDAL RESIN COMPOSITIONS FOR CONTROLLING SOIL BORNE PESTS AND PROCESS FOR THE PREPARATION THEREOF

This is a continuation of application(s) Ser. No. 08/239,850 now pending, filed on May 9, 1994 which is a divisional of Ser. No. 07/925,326 filed on Aug. 6, 1992, ABD., which is a continuation of Ser. No. 07/447,960 filed on Dec. 7, 1989, ABD., which is a continuation of Ser. No. 07/114,821 filed on Nov. 5, 1987 ABD., which is a continuation-in-part of 06/933,842 filed on Dec. 24, 1986 ABD.

BACKGROUND OF THE INVENTION

The present invention relates to safened solid pesticidal resin composition which previously exhibited toxic dermal effects of the active pesticide. Examples of the type of active ingredient safened in the present compositions include O,O-diethyl S-[[(1,1-dimethylethyl)thio]methyl] phosphorodithioate, also known as terbufos, and O,O-diethyl-S-(ethylthiomethyl)phosphorodithioate, also known as phorate. U.S. Pat. No. 2,586,655, issued to Hook on Feb. 19, 1952, generally discloses these compounds, and U.S. Pat. No. 2,596,076, issued to Hook on May 6, 1952, discloses terbufos, with U.S. Pat. No. 2,759,010, issued to Lorenz et al on Aug. 14, 1956 disclosing phorate.

Both terbufos and phorate are effective soil and systemic insecticide-nematicides and are commercially used throughout the world. Unfortunately, these compounds, although effective insecticide-nematicides, also are toxic to mammals if they should enter the mammal's circulatory system through ingestion, inhalation or dermal absorption. This toxicity is more apparent by the LD50 values of these compounds. The acute oral LD50 value in rats of phorate is 1.6–3.7 mg technical/kg and for terbufos, 1.6 mg technical/kg. The acute dermal toxicities in rats are 2.5–6.2 mg technical phorate/kg and 7.4 mg technical terbufos/kg animal. Likewise, the acute dermal toxicities on rabbits are 3.1–6.4 mg technical phorate/kg animal and 1.0 mg technical terbufos/kg anima.

It can be seen, therefore, that there is potential hazard for individuals exposed to handling the pesticides, such as terbufos and phorate, as well as other such pesticides with acute oral and/or acute dermal toxicities less than about 50 mg/kg. Those individuals involved in the manufacture, packaging, handling, transportation or use of such pesticides are at high risk of exposure to said toxic chemicals. The potential health safety problems associated with these pesticides have spurred attempts to improve the LD50 values of said pesticides and to provide compositions which exhibit better margins of safety than originally available. U.S. Pat. No. 4,059,700 issued to Lindsay on Nov. 22, 1977, relates to a process to improve the safety of terbufos. Montmorillonite clay is used as a carrier for terbufos and phorate. This composition provides a product with an LD50 dermal toxicity, on rabbits, of about 27–37 mg/kg. Thus, the dermal toxicity is 2 to 3 times less toxic than the compositions available prior to the Lindsay invention. U.S. Pat. Nos. 4,485,103 and 4,343,790, issued to Pasarela on Nov. 27, 1984 and Aug. 10, 1982, respectively, also improve the margin of safety of insecticide-nematicide compositions containing terbufos or phorate. Coating an inert sorptive or non-sorptive granular carrier impregnated or coated with terbufos or phorate with a finely divided sorptive substrate and an acrylic polymer provides a safer composition as evidenced by rabbit dermal LD50 values of about 40 and 80 mg/kg.

Even though these inventions improved the dermal toxicities of pesticides such as terbufos and phorate, an effective resin-type reduced toxicity pesticidal composition with residual activity and good biological activity was still needed. U.S. Pat. No. 4,554,155 issued to Allan et al on Nov. 19, 1985 discloses controlled-release compositions which may contain a wide variety of listed pesticides, including phorate. These controlled-release compositions specifically contain kraft lignin and a biodegradable water-insoluble organic polymer that releases the pesticide by structural disintegration of the outer surfaces. As such, these compositions are based on erosion of the matrix to control the release of pesticide. Exposure of the surfaces of those compositions to the environment results in the loss of the structural integrity of the polymer and/or fracture thereof. Therefore, new surfaces of the biologically active material-polymer are exposed to the environment for further release of the component.

Resins also are used in animal collars and tags to control a variety of ectoparasites which infest such animals. For instance, U.S. Pat. No. 4,150,109 issued to Dick et al on Apr. 17, 1979 discloses animal pesticidal collars containing diazinone or diazoxone, a solid macromolecular substance chosen from solid vinyl and vinylidene substances and a plasticizer. About forty organo-phosphates are listed for possible incorporation into these animal collars, but terbufos and phorate are not among the pesticides listed. This is not, however, altogether surprising since terbufos and phorate are soil and plant systemic insecticides and are extremely toxic to mammals.

Another animal collar containing a pesticide is disclosed in U.S. Pat. Nos. 4,134,977 and 4,158,051, issued to Greenberg on Jan. 16, 1979 and Jun. 12, 1979, respectively. The Greenberg collars are prepared with dimethyl 1,2-dibromo-2,2-dichloroethyl phosphate, commonly referred to as naled, a plasticized polyvinyl chloride, a substantially non-volatile carbamate and a surface porosity control agent such as chloro-acetaldehyde, chloral, bromoacetaldehyde, bromal or the like. Those compositions provide controlled release of the insecticide as a vapor to surround the animal and as a powder that migrates over the coat of the animal.

U.S. Pat. No. 4,198,782 issued to Kydonleus on Apr. 22, 1980, discloses a method for making polymeric controlled-release pesticides by granulating a laminated sheeting material comprising a non-porous polymeric sheet, a polymeric core film containing phorate or other insecticide and a second solid non-porous polymeric sheet adhered to the insecticide-containing polymeric core material. The thus-prepared sandwich is then chopped into granulated particles. Insect control is obtained with the granulated insecticide compositions prepared as described. However, unfortunately when the laminated materials are cut to the sizes necessary for use in the field, extended activity is lost and little or no safening appears to be achieved.

Other resin compositions are disclosed in U.S. Pat. No. 4,041,151 issued to Milionis et al on Aug. 9, 1977 and U.S. Pat. No. 4,145,409 issued to Paserela on Mar. 20, 1979. The preparation of insecticidal and acaricidal resin compositions formed into flexible collars for attaching to animals to protect said animals against attack and/or infestation by insects and acarids is disclosed in those two designed to deliver an insecticidal or acaridicidal agent having relatively low mammalian toxicity onto the coat and body of an animal. Pesticides with high mammalian toxicity are not listed for incorporation into resins, moreover, it is not suggested that such incorporation may provide a concentrate or composition with markedly improved safety.

Thus, although the above-described references provide phorate, terbufos and/or other pesticide compositions with reduced dermal toxicity and/or extended residual activity, the disclosed technology seems insufficient to lower the margin of safety or the oral and/or dermal LD50 values low enough to remove said pesticides from the hazardous pesticide catagory.

To add to the potential problem, PVC (polyvinyl chloride) compositions which contain highly toxic pesticidal agents are not particularly simple to produce and cannot be prepared by simple incorporation of the pesticide into the PVC. Bulk density for directed application is lacking and effective extended insect control, i.e. throughout the growing season, plus the necessary safety in handling of the finished product is not present.

SUMMARY OF THE INVENTION

The present invention provides a solution to these problems unanswered successfully by the state of the art by providing novel dry-blended extrudable pesticidal resin compositions and pelletized pesticidal resin compositions, in concentrate or finished product form, which combine enhanced safety, effective residual activity of the product and improved chemical stability of the pesticide in the finished products.

It is an object of the present invention, therefore, to provide pesticidal compositions and processes for the preparation thereof wherein said composition contains a highly toxic pesticidal agent, selected polyvinyl chloride resin having appropriate physical and chemical characteristics, selected plasticizers, selected resin stabilizers, lubricants and mineral additives. Surprisingly, these compositions provide an agronomically useful product which is characterized by non-dusting, markedly reduced mammalian toxicity, significantly increased bulk density, extended residual activity and improved pesticide stability.

It is an additional object of the present invention to provide pesticidal compositions, particularly compositions containing the toxic pesticides with low LD50, and to provide such pesticides in a form having significantly improved dermal mammalian toxicity, improved insecticidal-nematicidal activity and extended residual effectiveness.

A further object of this invention is to provide pesticidal compositions which provide a margin of safety otherwise not found in previously-available compositions containing said pesticides.

It is also an object of this invention to provide pesticidal compositions with improved dermal mammalian toxicity and containing multiple pesticidal agents that impart different types of biological activity to the locus of treatment.

These and other objects of the present invention will become more apparent by the detailed description of the invention provided hereinbelow.

DETAILED DESCRIPTION OF THE INVENTION

The present invention relates to safened pesticidal resin compositions for controlling soil borne pests and process for the preparation thereof. The novel safened resin compositions of the present invention are dry blended, extrudable resin compositions, extruded pesticidal resin compositions and pelletized pesticidal resin compositions comprising pesticide, the technical grade of said pesticide having a dermal LD50, measured on rats or rabbits, of less than 50 mg/kg. The invention also relates to the unique process for the preparation of the present safened pesticidal compositions.

The compositions of the invention are prepared either as concentrates or finished products. The concentrates are prepared by dry blending about 4.0% to 65%, preferably about 4.0% to 50%, by weight, or a pesticide having a dermal LD50, measured on rats or rabbits, of less than 50 mg/kg; and about 5.0% to 60%, by weight, of a polyvinylic resin having an average molecular weight of about 41,000 to 130,000 preferably about 50,000 to 69,000. Polyvinyl chloride suspension resin is an example of such a resin. Further, other examples of resins of the present compositions include polyvinyl acetate or polyvinyl alcohol resin. In addition, of a stabilizing agent or mixture of heat-stabilizing agents for the resin and about 0.0% to 2.0%, by weight, of a lubricant are included. Silicon dioxide or other sorptive agent is optionally added to the concentrate at levels of about 0.0% to 10.0%, preferably 0.0% to 2.0%.

Pesticides useful in the concentrates and finished products of the present invention include, but are not limited to, O,O-diethyl S-[[(1,1-dimethylethyl)thio]methyl] phosphorodithioate, (terbufos); O,O-diethyl S-(ethylthiomethyl)phosphorodithioate, (phorate); (±)-O-ethyl S-phenylethylphosphorodithioate, (fonofos); diethyl 1,3-dithiolan-2-ylidene phosphoramidate, (phosfolan); 2-methyl-2-(methylthio)propionaldehyde O-methyl-carbamoyloxine (aldicarb); O,O-diethyl 2-ethylthioethyl phosphorothioate (demeton); O-ethyl S,S-dipropyl phosphorodithioate (ethoprophos); O,O-diethyl O-2-pyrazinyl phosphorothioate (thionazin); 2,3-dihydro-2,2-dimethyl-7-benzofuranyl methylcarbamate, (carbo-furan);1-methylethyl-2[[ethoxy[(1-methylethyl)amino] phosphinothioyl]oxy]benzoate, (isofenphos); O,O-diethyl S-2-ethylthioethyl phosphorodithioate, (disulfoton); O,O-diethyl O-4-(methylsulfinyl)phenylphosphorothioate, (fensulfothion) and the like. Terbufos and phorate are especially preferred in the concentrates and finished compositions of this invention because both are excellent plasticizing agents, as well as superior soil and systemic pesticides.

These two compounds are highly effective for controlling soil borne insects and nematodes which attack the root systems of plants. They also are effective for controlling chewing and puncturing insects and arachnids which feed on the foliage or fluids of plants.

Although this invention is especially useful for improving the safety in handling of very toxic chemicals referred to hereinabove with acute oral or dermal LD50's, as measured on rats or rabbits, of 50 mg/kg or less, the invention also may be used to improve the safety in handling of other chemicals, also quite toxic, but which do not have an LD50 of 50 mg/kg. For example, compounds which have an acute oral or acute dermal toxicity of about 50 mg/kg to about 300 mg/kg, or even 500 mg/kg, can be prepared in accordance with the process of the present invention, with the benefits of enhanced safety and ease of handling. Chemicals in this category include chlorpyrifos, bufencarb, fenthion and the like.

Further, the pesticidal compositions of the present invention provide enhanced extended biological activity, thereby making application easier for the farmer.

Surprisingly, it has also been found that pesticides in the compositions of this invention, particularly the phosphate pesticides exhibit markedly improved chemical stability as compared to the conventional granular pesticide compositions.

Advantageously, the compositions of this invention are effective for controlling insects, nematodes and arachnids which feed on the root systems and foliage of plants when applied at about 0.25 to 10 kg/ha to the soil in close proximity to the propagating organ of a plant at planting time, such as in furrow.

Also, it has now been found that, in addition to the above-mentioned benefits derived from the compositions of the invention, one or more additional pesticides can be used to replace a portion of the mineral additive and for the secondary plasticizing agent of said compositions thereby providing safened pesticidal resin compositions with multiple and/or mixed biological efficacies.

The compositions of the invention can, thus deliver a multiplicity of biologically active agents including: control agents for soil borne pests, plant nutrients, plant systemic insecticidal and miticidal agents, herbicidal agents, plant growth regulating agents and the like.

The concentrate compositions of the present invention provide an effective and less hazardous manner for transporting highly toxic pesticides, i.e. pesticides with an oral and/or dermal LD50, measured on rats or rabbits, of less than 50 mg/kg. Although the pesticides useful in the present invention are among the most effective agents for controlling insects, arachnids and nematodes in the soil, particularly terbufos and phorate, they have LD50 as measured on rats or rabbits, of about 1.0 to 50.0 mg.tech/kg, thereby making manufacturing, handling, transporting and using these products a potential hazard. Therefore, extreme care to avoid contact or inhalation of the pesticides was always required.

The concentrates of the present invention are useful products and can have a significant impact on the agricultural industry. These concentrates provide an effective means for reducing dusting and inhalation problems and provide about a 5 to 10 fold margin of safety over the technical grade pesticides from which they are prepared. The present concentrates also provide about 2 to 2.5 fold margin of safety over the presently-marketed compositions containing said pesticides. Since these concentrates do not contain the mineral additives used in the preparation of the extruded and/or pelletized finished compositions of the invention, they have the added advantage of avoiding added shipping costs, which would be assessed against the increased weight and bulk of the mineral additives in the finished products.

Although the concentrates of this invention are useful and provide improved safety in handling of the product in comparison to technical grade pesticide, a finished composition is desired for distribution to farm products distributors, farmers and the like. These finished compositions are prepared in the form of extruded strips, strands, rods, sheets or as free flowing, uniform particulate compositions in which the particulate material may be characterized as dust free beads, granules, pellets, prills or the like.

To prepare the finished products from the above-described concentrates, the concentrate is introduced into a high intensity mixer, along with about 0.0% to 50%, by weight, preferably 0.2% to 25.0%, by weight, of a secondary plasticizing agent and about 20.0% to 80.0%, by weight, and preferably about 20.0% to 55.0%, by weight, of a mineral additive. The mixture is blended at an elevated temperature, cooled, passed to an extruder where it is heated to a temperature of about 160° C., extruded and then pelletized.

When dry blending is needed in the process of the present invention, the concentrate, mineral additives and secondary plasticizing agents are blended using a high intensity mixer-cooler, conducted at temperatures of about 75° C. to 110° C.

When blending is complete, the mixture is cooled to about 70° C. and passed to an extruder or melt pump. This is then heats the mixture to a temperature of about 150° C. to 180° C., preferably about 155° C. to 160° C. The extruder forces the molten polymer mixture through a die having a series of holes, preferably in a circular pattern. As the polymer emerges from the die holes, it is cut into pellets by rotating blades and permitted to solidify as the pellets pass through the cutting chamber. The pellets are picked up in the cutting chamber by a stream of water which transports them to a tempered water system where they are dried and discharged from the drier. The pellet water is then filtered, pressurized, cooled and recirculated to the pelletizer by the tempered water system.

Use of this system for the preparation of the compositions of the present invention is important since it provides an essentially closed system for handling the toxic pesticidal materials. This system eliminates dusting problems and captures any toxicant technical pesticide which may adhere to the surface of the pelleted compositions. Thus, potential environmental pollution problems encountered in the manufacture of convention pesticidal formulations by conventional methods are avoided.

While the compositions of the present invention can first be prepared as concentrates and then further processed to yield finished compositions, a preferred method for preparing the finished compositions involves dry blending about 5% to 60%, based on the weight of the finished product, of a polyvinylic resin with about 20% to 80%, preferably 20% to 55%, by weight of a mineral additive, about 0.2% to 1.5%, preferably 0.2% to 1.0%, by weight, of a stabilizing agent or mixture of stabilizing agents for the resin and about 0.1% to 1.0%, by weight, of a lubricant. After dry blending the mixture of resin, mineral additive, stabilizer and lubricant, the blended mixture is introduced into a high intensity mixer where it is admixed with about 1% to 30%, by weight, of the pesticide, 0.0% to 50%, by weight, preferably 0.2% to 25.0%, by weight, of a secondary plasticizing agent and about 0.2% to 1.5% of a stabilizing agent. The pesticide, secondary plasticizing agent and stabilizing agent, preferably epoxidized soybean oil, are generally in liquid form.

The mixture then is subjected to high intensity mixing, and the temperature of the mixture is heated to about 75° C. to 110° C. The mixture is then quickly cooled and charged into an extruder where it is heated to about 150° C. to 180° C. and extruded as a ribbon, strip, rod, strand or the like. The extruded ribbon or strand is then introduced into a pelletizer where it is formed into small spheres, pellets or beads.

In the preferred process, the pellets are then introduced into a water transport system in the event that toxicant pesticide adheres to the surface of the particles. This water transport system thus serves to wash the outer surfaces of the particles, trap any toxicant pesticide adhering thereto and prevents escape of toxicant pesticide into the atmosphere. The water is then separated from the pelletized product, and the pellets are dried and screened or sieved to obtain product of the desired pellet size.

Among the pesticides employed in the novel compositions of the present invention are terbufos, phorate, aldicarb, demeton, ethoprophos, thionazin, fonofos, phosfolan, carbofuran, isofenphos, chlorpyrifos, disulfoton, fensulfothion, bufencarb, fenthion, with terbufos and phorate preferred.

Polymers useful in the compositions of the present invention include polyvinyl chloride resins, particularly polyvinyl chloride suspension resin, polyvinyl acetate and polyvinyl alcohol. These polymers having a weight average molecular weight of about 41,000 to 130,000, preferably 50,000 to 69,000. The polymers of the invention are available from a variety of polymer manufacturers, such as Gerorgia Gulf Corporation, which offers the following PVC resins:

| Resin # | Molecular Weight |
|---------|------------------|
| PVC 1055 | 41,000 |
| PVC 1060 | 50,000 |
| PVC 1070 | 66,000 |
| PVC 1073 | 69,000 |
| PVC 2073 | 69,000 |
| PVC 1079 | 75,000 |
| PVC 1082 | 89,000 |
| PVC 1091 | 102,000 |
| PVC 1095 | 110,000 |
| PVC 1010 | 123,000 |
| PVC 1110 | 130,000 |

Among the secondary plasticizers useful in the preparation of the compositions of this invention are the organic phthalates, such as butyl benzyl phthalate octyl epoxytallate and diisononyl phthalate, organic phosphates such as tricresyl phosphate, epoxidized soybean oil, epoxidized linseed oil, epoxidized butyl esters of tall oil, organic trimellitates, such as trioctyl mellitate and organic citrates such as acetyl tributylcitrate, or mixtures thereof.

Useful stabilizing agents effective for stabilizing the resin include stearates, such as zinc/calcium stearates, alkaline earth metal stearate, epoxidized soybean oil, secondary octyl tins and phosphites and organo barium and cadmium complexes, or mixtures thereof.

Typical mineral additives used in the compositions of the present invention include barium sulfate, calcium sulfate, calcium carbonate, clays such as kaolin, bentonite, attapulgite and montmorillonite, cellulose products, mica, wallstonite and fertilizers such as dicalcium phosphate, tricalcium phosphate and the like, or mixtures thereof.

These mineral additives, especially the alkaline earth metal sulfates and carbonates, are essential components of the extruded and extruded-pelletized products of this invention. While not wanting to be limited by theory, it is believed these mineral additives impart the bulk density to the extrudates that permits the directed application into the furrows or beside the planted crops which they are to protect, thereby inhibiting the movement of the extrudates by wind or rain from the locus of their application. These mineral additives also are believed to be instrumental in providing relatively uniform and extended release of the pesticide from the extrudate and in aiding the decomposition of the extrudates in the soil when the growing season is finished.

Lubricants useful in the present invention to improve the extrudability of the compositions include calcium, magnesium, aluminium and glycerol mono stearate, stearic acid, paraffin waxes, low molecular weight polyethylene and the like.

Since it has now been found that several of the above-said pesticides used in the compositions of the present invention are plasticizing agents as well as pesticidal agents, when preparing polyvinylic resin compositions of the invention containing pesticide-plasticizing agents, the amount of secondary plasticizing agent required for an extrudable composition can frequently be limited to as little as 2% to 10% of the weight finished extruded product. It has also been found that a number of other pesticidal agents including: herbicidal, insecticidal and nematicidal agents, such as 2-chloro-N-(2,6-diethyl-phenyl)-N-(methoxymethyl) acetamide (alachlor) and O,O-dimethyl S-methylcarbamoylmethyl phosphorodithioate (dimethoate) can be substituted for the conventional secondary plasticizing agents described below and employed in the preparation of the extruded and extrudable compositions of the invention. As such, the resulting extrudates can impart to the locus of treatment not only soil insect and nematode control but also weed control, systemic protection of plants from leaf feeding insects, or broad spectrum insect control depending upon the pesticide substituted for the secondary plasticizing agent.

Flow Diagram I provides a graphical illustration of the hereinabove described process of manufacture.

FLOW DIAGRAM I

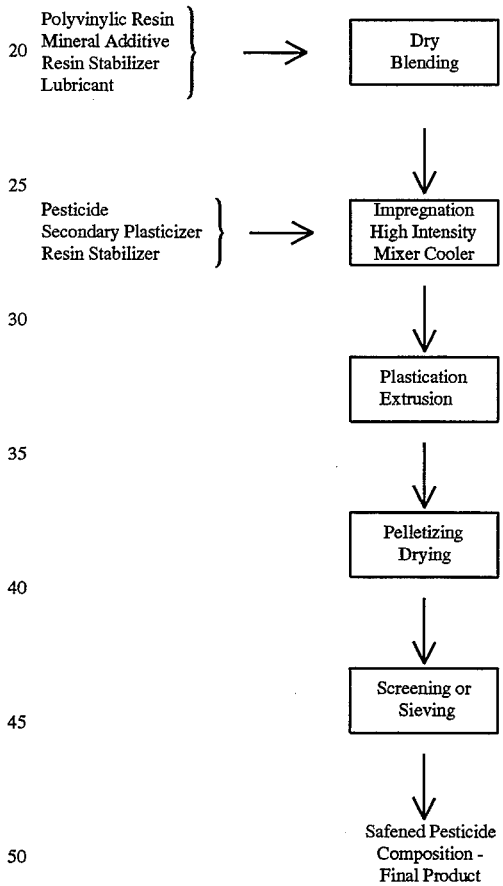

The apparatus useful in the dry blending aspects of the process of the present invention include high torque intensive mixers and low torque continuous ribbon blenders, both with heat-cool capabilities. The dry blend is prepared by charging the vinyl resin, dry stabilizer (Ca/Zn Stearate) and filler to a mixer heated to 70° C. The blend is premixed for 5 minutes. The liquid portion is weighed and charged to a millipore pressure vessel heated to about 70° C. (The liquid portion consists of the plasticizer, active ingredient and liquid stabilizers). The dry blend is tumbled at a moderate rate with the liquid portion added over a five minute period. The entire mass is then heated to about 100° C. After adding the liquid, the blend should be free flowing. If not, a small amount of $SiO_2$ i.e. an amount of up to about 10.0%, generally 1.0% to 2.0%, is added. The entire mix is cooled and poured into a special sealable drum or pumped into an extruder, where the composition is compacted and extruded in a spagetti-like (i.e. strand or rod-like) sheet-like or ribbon-like form. This is then pelletized using an under water pelletizing system. A hot face air cooled system may, of course, be substituted for the under water pelletizer.

The finished products prepared as described above provide a great advantage because they have an increased bulk density of 45 to 100 pounds per cubic foot, generally 50–80 pounds per cubic foot compared to the commercially-available terbufos or phorate clay granulars of 31–40 pounds per cubic feet. This allows the farmer to carry more product per load than could be carried if the product were formulated as a conventional granule. Transportation of more active ingredient per load by truck, tractor, or air delivery is therefore facilitated by the novel formulation of the present invention.

The products of this invention also are more stable to attrition. Since terbufos and phorate both pose potential severe inhalation hazards, with LD50s of 35 mg/kg body weight, reduction or elimination of product dusting and/or release of toxicant pesticide vapor is a safety advantage. Furthermore, the dust particles, even if formed during the process of the present invention, are less hazardous because of their improved dermal property.

Additionally, the present processing technology utilizes extrusion techniques of a continuous closed system process using state of the art technologies, thereby eliminating many manufacturing safety and handling problems.

The present invention is illustrated by the following examples which are illustrative and not limitative thereof.

EXAMPLE 1

Polyvinyl chloride suspension resin for preparation of safened terbufos pellets using placebo study technique with Lindgi-Littleford high intensity mixer and standard PVC/plasticizing technique In these tests the plasticizing agent tricresyl phosphate is substituted for terbufos, O,O-diethyl S-[[(1,1-dimethylethyl) thio]methyl]phosphorodithioate.

The composition is prepared by dry mixing at a temperature of 110° C. for about 5 minutes 18%, by weight, of Georgia Gulf PVC 1060, having a weight average molecular weight of 50,000, 55%, by weight, of barium sulfate and 1.0% by weight, of calcium stearate/zinc stearate resin stabilizer. To this mixture is added 9.0%, by weight, of tricresyl phosphate, which is the terbufos placebo substitute. Tricresyl phosphate is selected as the terbufos substitute because, like terbufos, it is a plasticizing agent. Also added are 15%, by weight, of the secondary plasticizing agent, butyl benzyl phthalate, and 2%, by weight, of the stabilizing agent, epoxidized soybean oil. The mixture is stirred for about five minutes at 100° C. Silicon dioxide (0.5% by weight) is then added, and the mixture is stirred for about 1 minute. This yields a freely flowable particulate composition having an average particle size of about 10 to 30 mesh.

The above procedure is also used for blending together 18%, by weight, of the Georgia Gulf PVC 1060, 55% by weight of barium sulfate, and 1.0% by weight of calcium/zinc stearate of a temperature of about 110° C. for about 8 minutes and then slowly admixing therewith 18% by weight of tricresyl phosphate, 6% by weight of butyl benzyl phthalate and 2.0% by weight of epoxidized soybean oil. This procedure provides a free flowing particulate composition suitable for extrusion.

Other compositions prepared in the same manner and then extruded are reported hereinbelow. Extrusion is conducted at a temperature of about 130° to 140° C. The extruded product is in the form of smooth, dust free, uniform strands.

| Ingredient | % By Weight |
| --- | --- |
| PVC-MW 50,000 | 25 |
| Ca/Zn Stearate | 1 |
| CaSO$_4$ | 49 |
| Tricresyl Phosphate | 3 |
| Butyl Benzyl Phthalate | 20 |
| Epoxidized Soybean Oil | 2 |
| | 100% |

Extruded product in the form of long strands is essentially dust free.

| Ingredient | % By Weight |
| --- | --- |
| PVC-MW 50,000 | 14 |
| BaSO$_4$ | 58 |
| Ca/Zn Stearate | 1 |
| Tricresyl Phosphate | 8 |
| Butyl Benzyl Phthalate | 18 |
| Epoxidized Soybean Oil | 1 |
| | 100% |
| Dry blend for extrusion. | |
| PVC-MW 50,000 | 25 |
| Ca/Zn Stearate | 1 |
| BaSO$_4$ | 49 |
| Tricresyl Phosphate | 3 |
| Butyl Benzyl Phthalate | 20 |
| Epoxidized Soybean Oil | 2 |
| | 100% |

Extrudate is in the form of long uniform strands.

EXAMPLE 2

Safened polyvinyl chloride suspension resin composition containing terbufos and prepared by the procedure of Example I Polyvinyl chloride, Ca/Zn stearate and CaSO$_4$ are blended as described in Example I above, but the blended composition is warmed to 70° C. Terbufos, butyl benzyl phthalate and expoxidized soybean oil are then added slowly and blended at 70° C. Addition of 0.05% by weight of SiO$_2$ to the blended mixture gives a free flowing composition which is readily extended at 140° C. to give the desired product.

| Ingredient | % By Weight |
| --- | --- |
| PVC-MW 50,000 | 25 |
| Ca/Zn Stearate | 1 |
| CaSO$_4$ | 49 |
| Terbufos | 17 |
| Butyl Benzyl Phthalate | 7 |
| Epoxidized Soybean Oil | 1 |
| | 100% |

EXAMPLE 3

Safened terbufos polyvinyl chloride suspension resin composition

Following the procedure of Example 1, polyvinyl chloride with a weight average molecular weight of about 50,000 is blended with barium sulfate at a temperature of about 110° C. To this mixture is then added diisononyl phthalate plasticizing agent and terbufos, O,O-diethyl S-[[(1,1-dimethylethyl)thio]methyl]phosphorodithioate. After blending, the mixture is cooled and passed to an extruder where the mixture is heated to 135° C. for eight minutes and then extruded. The extrudate, when evaluated for dermal toxicity, has an LD50 dermal toxicity, measured on rabbits, of 160 mg/kg.

The composition described above contains:

FORMULA A

| Ingredient | % By Weight |
|---|---|
| PVC-MW 50,000 | 14 |
| BaSO$_4$ | 60 |
| Terbufo | 18 |
| Diisononyl Phthalate | 8 |
| | 100% |

The above procedure is repeated with the ingredients indicated in Formula B to form the following composition:

FORMULA B

| Ingredient | % By Weight |
|---|---|
| PVC-MW 50,000 | 14 |
| BaSO$_4$ | 60 |
| Terbufos | 18 |
| Tricresyl Phosphate | 8 |
| | 100% |

This composition is blended, mixed, cooled, heated and extruded as described above, and the extrudate is found to have an LD50 dermal toxicity, measured on rabbits, of 180 mg/kg. As such, the above compositions have about a 4 fold improvement in the margin of safety over the commercially available terbufos granular products, which have an LD50, measured on rabbits, of about 35–40 mg/kg.

EXAMPLE 4

Safened terbufos polyvinyl chloride suspension resin compositions

In these evaluations, polyvinyl chloride suspension resin having a weight average molecular weight of 50,000 is dry blended with barium sulfate at room temperature (25° C.). To this mixture is added a mixture of terbufos and butyl benzyl phthalate. Thereafter, the thus-prepared mixtures are oven cured at 135° C., and the rabbit dermal toxicities of the compositions determined. The compositions evaluated are as follows:

| Ingredient | % By Weight |
|---|---|
| PVC-MW 50,000 | 14 |
| BaSO$_4$ | 60 |
| Terbufos | 18 |
| Butyl Benzyl Phthalate | 8 |
| | 100% |

The rabbit dermal LD50 for this composition is 320 mg/kg.

EXAMPLE 5

Safened polyvinyl chloride resin compositions pelletized to 18 to 48 mesh particle size Following the procedures of Examples 1–3 above but pelletizing the extruded compositions provides non-dusting, resilient 18–48 mesh pellets containing 17% to 23% by weight of terbufos and having dermal LD50's on rabbits, of about 130 mg/kg to 500 mg/kg. The pelletized product densities are about 60 and 90 lbs/ft$^3$.

The compositions evaluated are described below.

| Ingredient | % W/W | | |
|---|---|---|---|
| | 1 | 2 | 3 |
| PVC-MW 50,000 | 25 | 12 | 25 |
| Ca/Zn Stearate | 1 | 0 | 1 |
| BaSO$_4$ | 49 | 59 | — |
| CaSO$_4$ | — | — | 49 |
| Epoxidized Soybean Oil | 1 | 0 | 1 |
| Butyl Benzyl Phthalate | 7 | 6 | 7 |
| Terbufos (86.9%) | 17 | 23 | 17 |
| | 100% | 100% | 100% |

1) LD50 rabbit dermal 320 mg/kg, product assay 15% terbufos;
2) LD50 rabbit dermal 299 mg/kg, product assay 19.4% terbufos;
3) LD50 rabbit dermal 130 mg/kg, product assay 15% terbufos.

Biological evaluation of compositions 1,2 and evaluated against southern armyworm shows 100% control of these pests for 10 weeks.

Dermal toxicity of compositions of the present invention are determined by the following procedure using male albina rabbits as the test animals.

Materials

Five male albino rabbits weighing approximately 2.2 to 3.5 kilograms are selected for each dosage level. The hair is shaved from the entire trunk. Saran tubing or "Vinylite" film, VU 1900, 12 inches wide, 0.04 millimeters thick and of suitable length to fit around the rabbit is used. One felt cloth bandage measuring approximately 9×18 inches is used and four pieces of 1½ inches adhesive tape approximately 14 inches long are used.

Procedure for Solid Materials

The granular composition to be tested is placed in the center of the plastic film and is moistened with water. The rabbit's underside is moistened with water, and the animal is placed belly down on the material. The plastic film is then brought up and around the animal and secured at each end with strips of adhesive tape. The felt cloth is then placed under the belly and brought up and around the animal and secured to the body with the remaining two strips of adhesive tape.

Procedure for Liquid Materials

The animal is placed on the plastic film and wrapped, and the film secured with adhesive tape. The test material is then injected under the plastic with an appropriate size needle and syringe. Then, the felt cloth is placed under the belly and brought up around the animal and secured with the two remaining strips of adhesive tape. This forms a "cuff".

Evaluation

Twenty-four hours after dosing, the "cuff" is removed, and any remaining material is brushed away. If the material cannot be removed, the animal is fitted with a fiber collar which prevents the animal from licking the treatment area. The animals are observed for 14 days, postdosing, noting signs of toxicity, skin irritation and mortality. At the end of the 14 days, the animals are sacrificed and weighted.

By the above procedure, the dermal toxicities of the compositions described in Examples 3–5 above are determined.

EXAMPLE 6

Biological evaluations of extruded, pelletized PVC terbufos compositions

The following studies were undertaken to compare the initial and residual performance against 3rd instar *Diabrotica undecimpunctata howardi* larvae for various types of PVC granular formulations of terbufos, as compared to the standard 15 formulation.

In all studies, the dosage of the toxicant pesticide is calculated on the basis of the field practice of banding granules in a 7 inch band over the row. Residue studies indicate that terbufos remains in the top 3 inches of soil through the corn growing season. The dosage for terbufos 15G Systemic Insecticide-Nematicide is 8 oz of formulation per 1000 feet of row. Therefore, the volume of soil in 1000 feet by 7 inches by 3 inches is calculated and converted to liters. The amount of active pesticide in that volume is determined and then reduced to the amount required for 1 liter of soil. Finally, all dosages are converted to kg/ha equivalents.

The soil for the study is subsampled to make moisture determinations. Initially, the determinations are made by oven drying the samples and weighing them. In later studies, an Aquatest II Photovolt (New York City, N.Y.) is used to measure soil moisture. Since 15% moisture is optimum for larval survival, an attempt is made to maintain that level during the bioassays.

The appropriate amounts of formulation are added to 1 liter of soil which had been placed into 4 ml polyethylene bags. The bag is then put into a tumbler and tumbled for 3–5 minutes to provide a uniform mixture of soil and toxicant pesticide. The soil is stored in those polyethylene bags for the duration of the experiment and held at 27° C. Different soils used in the studies are identified hereinbelow.

The bioassays are set up by placing 25 ml of the treated soil into 30 ml wide-mouth screw top glass jars. About 1 cc of millet seed is added to the soil as food for the insects. The jar is capped, and the soil and seed are thoroughly mixed on a vortex mixer. After mixing, 10 southern corn rootworms about 6–8 days old, are placed into the jar. The jar is capped loosely and held at 27° C. for 7 days. After 7 days, the soil is removed from the jars and examined for live larvae. Missing larvae are presumed dead since dead larvae decompose very rapidly.

TABLE I[1]

| | | | Soil: Silt loam from Atlantic, Iowa | | | |
|---|---|---|---|---|---|---|
| No. | % Granular Formulation | Preparation | Dose Kg/Ha | Ingredients | % W/W | Mg Formulation/L Soil |
| 1 | Terbufos 15.0 | Example 3 Formula B | 0.25 | Terbufos PVC TCP BaSO$_4$ | 18 14 8 60 | 12.50 |
| 2 | Terbufos 18.8 | Example 5 Formula 2 | 0.25 | Terbufos PVC BBP BaSO$_4$ | 23 12 6 59* | 9.95 |
| 3 | Terbufos 15.0 | Example 3 Formula A | 0.25 | Terbufos PVC DINP BaSO$_4$ | 18 14 8 60 | 12.50 |
| 4 | Terbufos 15.0 | (Standard) Commercial product | 0.25 | | | 12.50 |
| 5 | CHECK Untreated | | | | | |

[1]Soil is slit loam from Atlantic, Iowa to simulate prairie soil
*Fused at 275 deg. F.

The Atlantic, Iowa soil used in this test simulates prairie soils commonly found in the cornbelt. Possibly, this soil reduces the time required to detect a break in biological activity of the formulations. This soil is not sterilized. The results are provided in Table II.

TABLE II[1]

Terbufos PVC Study
Percent mortality to third instar *Diabrotica undecimpunctata howardi*

| Formulation | Preparation | Dose Kg/ha | 1 | 2 | 4 | 7 | 8 | 10 | 12 | 14* | 15 | 17 | 18* |
|---|---|---|---|---|---|---|---|---|---|---|---|---|---|
| Terbufos 15.0 g | Ex 3 - B | 0.25 | 90.0 | 100.0 | 100.0 | 100.0 | 100.0 | 100.0 | 95.0 | 96.4 | 97.5 | 100.0 | 100.0 |
| Terbufos 18.8 g | Ex 5 - 2 | 0.25 | 100.0 | 100.0 | 100.0 | 95.0 | 92.5 | 100.0 | 100.0 | 100.0 | 100.0 | 100.0 | 100.0 |
| Terbufos 15.0 g | Ex. 3 - A | 0.25 | 77.5 | 100.0 | 97.5 | 100.0 | 100.0 | 100.0 | 95.0 | 100.0 | 100.0 | 100.0 | 94.1 |
| Terbufos 15 g | Standard | 0.25 | 100.0 | 100.0 | 100.0 | 100.0 | 100.0 | 92.5 | 95.0 | 96.4 | 87.5 | 7.5 | 55.9 |
| Check | — | — | 10.0 | 7.5 | 7.5 | 7.5 | 12.5 | 12.5 | 7.5 | 0.0 | 12.5 | 7.5 | 0.0 |

[1]Soil is slit loam from Atlantic, Iowa
*Abbott's formula calculated on these data due to check mortality in excess of 15%

All of the formulations, including the standard, release well during the first week of the study, except example 3-A which requires 2 weeks to become fully effective. The standard 15 G formulation performs poorly (under 90% mortality) by the 15th week of the study. All of the extruded granular formulations are 94% to 100% effective through 18 weeks. Thus, all of the experimental formulations give residual persistence superior to that of the standard in this study.

Study 2 is a duplicate of study 1 except for the soil. The objective is to compare the time required for a break in biological activity of the formulations with the use of sterilized versus non-sterilized soils.

In the sterilized soil, example 3-B took 3 weeks to produce 100% mortality. However, it remains highly effective for 20 weeks. Example 3-A has a delayed release of 1 week initially and provides 100% control through 14 weeks at which time its activity drops below an acceptable level. The standard 15 G formulation is effective until the 20th week after treatment in this study. Example 5-2 appears to outlast the standard, but, it must be noted that the depletion of treated soil at last sampling reduces the number of replications by half. Thus, the conclusion that Example 5-2 is equal or superior to the standard in sterilized soil may not be justified in this case.

16 parts of butyl benzyl phthalate. The mixture is heated to a temperature between 45° and 50° C. and stirred continuously. This yields true solutions of the active ingredients in the mixtures. A uniform blend of calcium/zinc stearate stabilizer 0.9–1.0 parts, PVC 2073 molecular weight average molecular weight 69,000 22.47 to 23 parts and anhydrous calcium sulfate 44 to 49 parts, is blended and added to the previously prepared solution of pesticide, epoxidized soybean oil and butyl benzyl phthalate, and mixed to a uniform paste. The mixture is heated to 65° to 75° C. and stirred until a uniform free-flowing dry powder is produced.

In these preparations carbofuran and aldicarb do not dissolve completely. Therefore sufficient methylene chloride is added to produce the true solution. Thereafter the blend of calcium/zinc stearate, PVC and calcium sulfate is added to the pesticide solution and the mixture stirred. These mixtures with methylene chloride are heated to evaporate said methylene chloride. The resulting mixture is heated to 65° to 75° C. and stirred until a dry free-flowing powder is formed.

The thus prepared compositions are then introduced into a melt index apparatus which is preheated to 155° to 160° C. Ten gram increments are extruded in the form of a strand 2 mm in diameter. The strands are extruded into water in a beaker, then removed and dried. The extruded strands are then cut in one inch sequrents and then ground in a krups

TABLE III

Percent mortality to third instar *Diabrotica undecimpunctata howardi*

| Formulation | Preparation | Dose Kg/ha | 1* | 2 | 3 | 5 | 7 | 9 | 12 | 14 | 15 | 17 | 18 | 19 | 20 |
|---|---|---|---|---|---|---|---|---|---|---|---|---|---|---|---|
| Terbufos 15.0 g | Ex. 3 - B | 0.25 | 0.0 | 77.5 | 100.0 | 100.0 | 100.0 | 100.0 | 100.0 | 97.5 | 100.0 | 97.5 | 100.0 | 100.0 | 100.0 |
| Terbufos 18.8 g | Ex. 5 - 2 | 0.25 | 100.0 | 100.0 | 100.0 | 100.0 | 100.0 | 100.0 | 100.0 | 97.5 | 92.5 | 97.5 | 95.0 | 82.5 | 100.0** |
| Terbufos 15.0 g | Ex. 3 - A | 0.25 | 57.5 | 100.0 | 100.0 | 100.0 | 100.0 | 100.0 | 100.0 | 67.5 | 57.5 | 70.0 | 75.0 | 77.5 | 32.5 |
| Terbufos 15 g | Standard | 0.25 | 100.0 | 100.0 | 100.0 | 100.0 | 100.0 | 100.0 | 100.0 | 85.0 | 90.0 | 97.5 | 95.0 | 97.5 | 55.0 |
| Check | — | — | 0.0 | 12.5 | 2.5 | 7.5 | 5.0 | 12.5 | 17.5 | 15.0 | 7.5 | 5.0 | 2.5 | 5.0 | 15.0 |

*Abbott's formula calculated on these data due to check mortality in excess of 15% except when all values = 100%.
**Last sample consists of two replicates due to shortage of treated soil.

EXAMPLE 7

Preparation of extruded, pelletized PVC soil insecticide compositions

In these tests the compositions are prepared by admixing about 15 to 17 part by weight of a toxic soil insecticidal agent with about 1 part of epoxidized soil bean oil and 11 to coffee mill and screened to obtain the 20/50 mesh particles. The compositions thus prepared are reported in table IV below. Particle size distribution of the screened particles are reported in Table V. The extruded compositions thus prepared have been submitted for acute oral and/or acute dermal toxicity determinations.

TABLE IV

Extruded Compositions

| Ingredients | Concentration as % W/W | | | | | |
|---|---|---|---|---|---|---|
| | A | B | C | D | E | F |
| 1. *a) Carbofuran | 15.0 | | | | | |
| b) Aldicarb | | 15.0 | | | | |
| c) Chlorpyrifos | | | 15.0 | | | |
| d) Fenvalerate | | | | 15.0 | | |
| e) Ethoprophos | | | | | 16.67 | |
| f) Fonofos | | | | | | 16.67 |
| 2. Epoxidized Soy Oil | 1.0 | 1.0 | 1.0 | 1.0 | 1.0 | 1.0 |
| 3. Butyl Benzyl Phthalate | 16.0 | 16.0 | 11.0 | 11.0 | 11.0 | 11.0 |
| 4. Calcium, Zinc Stabilizer | 0.9 | 0.9 | 1.0 | 1.0 | 0.98 | 0.98 |
| 5. PVC 2073 | 23.0 | 23.0 | 23.0 | 23.0 | 22.48 | 22.47 |
| 6. CaSO$_4$, Anhyd. | 44.1 | 44.1 | 49.0 | 49.0 | 47.87 | 47.88 |

*IUPAC chemical names are:
1A: 2,3-dihydro-2,2-dimethylbenzofuran-7-yl methylcarbamate.
1b: 2-methyl-2-(methylthio)propionaldehyde O-methylcarbamoyloxime.
1c: O,O-diethyl O-3,4,6-trichloro-2-pyridyl phosphorothioate.
1d: (RS)-a-cyano-3-phenoxybenzyl (RS)-2-(4-chlorophenyl)-3-methylbutyrate.
1e: O-ethyl S,S-dipropyl phosphorodithioate.
1f: O-ethyl S-phenyl(RS)-ethylphosphonodithioate.

TABLE V

Screen Analyses

| U.S. Sieve Number | 24/48 Creek-O-Nite Check | Percent Retained On | | | | | |
|---|---|---|---|---|---|---|---|
| | | A | B | C | D | E | F |
| 16 | 0.0 | 0.08 | 0.09 | 0.18 | 0.09 | 0.0 | 0.0 |
| 20 | 1.0 | 9.59 | 9.08 | 5.77 | 17.45 | 2.997 | 0.99 |
| 30 | 41.0 | 53.83 | 51.02 | 50.79 | 52.91 | 66.60 | 70.50 |
| 40 | 38.5 | 24.50 | 26.63 | 27.26 | 20.36 | 22.08 | 21.23 |
| PAN | 19.5 | 12.00 | 13.18 | 16.00 | 9.19 | 8.35 | 7.28 |

TABLE VI

Toxicity Testing on 15% Pelleted Compositions

| | Technical | | PVC Pelleted Compositions | |
|---|---|---|---|---|
| Ingredient | Rat Oral LD50 (mg/kg) | Rabbit Dermal LD50 (mg/kg) | Rat Oral LD50 (mg/kg) | Rabbit Dermal LD50 (mg/kg) |
| Carbofuran | 11 | 10,200 | 100 | — |
| Aldicarb | 0.9 | 5 | <12.5 | >120 |
| Chlorpyrifos | 96–270 | 2000 | >500 | — |
| Fenvalerate | 3200 | 2500 | — | — |
| Ethoprophos | 62 | 2.4 | — | 200 |
| Fonofos (Dyphonate) | 3 | 25 | >100 | >400 |

EXAMPLE 8

Combinations of Terbufos and Alachlor and/or Atrazine in PVC compositions

Safened pesticidal resin compositions for simultaneously controlling soil borne pests and undesirable weed species are prepared by the procedure of Example 7, excepting that the secondary pesticides, i.e. alachlor and/or atrazine aye dissolved or dispersed in terbufos before the terbufos is added to the mixture.

The compositions are prepared and extruded in accordance with the procedures of Example 7 and have the % concentrations reported in Table VII below.

TABLE VII

| Ingredient | Concentration as % w/w | | | | |
|---|---|---|---|---|---|
| | A | B | C | D | E |
| Terbufos, technical (87% Real) | 11.50 | 11.50 | 5.75 | — | — |
| Alachlor (99% Real) | 20.20 | — | 10.10 | 20.20 | — |
| Atrazine, technical (95% Real) | — | 21.00 | 10.53 | — | 21.00 |
| Epoxidized Soybean Oil | 1.00 | 1.00 | 1.00 | 1.00 | 1.00 |
| Butyl Benzyl Phthalate | 3.00 | 19.50 | 10.00 | 14.00 | 32.00 |
| PVC 2073 | 23.00 | 23.00 | 23.00 | 23.00 | 23.00 |
| Ca/Zn Stearate | 1.00 | 1.00 | 1.00 | 1.00 | 1.00 |
| Anhydrous Calcium Sulfate | 40.30 | 23.00 | 38.62 | 40.80 | 22.00 |

Alachlor is 2-chloro-2',6'-diethyl-N-(methoxymethyl)-acetanilide (IUPAC nomenclature. Atrazine is 2-chloro-4-ethylamino-6-isopropylamino-1,3,5-triazine (IUPAC nomenclature).

Compositions D and E are used as controls to determine whether alachlor and/or atrazine are herbicidally effective when utilized in alone and/or in the presence of terbufos in the PVC compositions of the invention.

It has now been observed that alachlor is quite soluble in terbufos and can be substituted for at least a portion of the secondary plasticizer in the compositions.

Atrazine is less soluble than alachlor in terbufos. This is evidenced by composition E where 32% of butyl benzyl phthalate is required to provide a satisfactory extrudate. Composition B containing 11.5% w/w of terbufos and 21% w/w of atrazine required only 19.5% w/w of the secondary plasticizer butyl benzyl phthalate. The extrudate B (viewed in cross section by microscope) reveals a shiny plasticized or fused surface, but the interior is less well fused.

Herbicidal evaluations of compositions A–E all show herbicidal control of undesirable plant species. Compositions A–C with terbufos plus alachlor and/or atrazine also provide soil insect control.

EXAMPLE 9

Preparation and evaluation of terbufos 15% granular compositions (See Example 12), 15% PVC granular resin composition and 20% PVC granular resin compositions Following the procedures of examples 1–3 above and then pelletizing the resulting compositions by the process illustrated in Flow Diagram I, yields extruded 15% and 20% terbufos PVC granular compositions and a 20% phorate PVC granular composition. These compositions have the concentrations reported in Table VIII below.

TABLE VIII

| Ingredient | Concentration % w/w | | |
|---|---|---|---|
| | A | B | C |
| Terbufos (87% Real) | 17.2 | 23.0 | — |
| Phorate (89.9% Real) | — | — | 23.0 |
| PVC 2073 | 17.2 | 23.0 | 23.0 |

TABLE VIII-continued

| | Concentration % w/w | | |
|---|---|---|---|
| Ingredient | A | B | C |
| Butyl Benzyl Phthalate | 3.5 | 3.5 | 3.0 |
| Mixed Mono Glycerol Stearates | 0.5 | 0.5 | — |
| CaSO₄ Anhydrous | 59.6 | 48.0 | — |
| BaSO₄ | — | — | 49.0 |
| Ca/Zn Stearate | 1.0 | 1.0 | 1.0 |
| Epoxidized Soy Oil | 1.0 | 1.0 | 1.0 |
| | 100.0 | 100.0 | 100.0 |

For evaluation of the above-described terbufos and phorate PVC resin compositions field studies are conducted using the commercially available terbufos and phorate compositions as standards.

A series of field trials are conducted at farms and universities to evaluate the above-said compositions for controlling corn rootworms and evaluating the compositions for phytotoxicity on grain sorghum.

In the phytotoxicity evaluations grain sorghum is planted in rows 0.9 meters apart and 15 meters in length. Four rows per plot are used and each treatment is replicated 3 times. The test compositions are introduced into the furrow at the time of planting at the rate of 1.12 to 2.24 kg/ha. At intervals of from 14 to 72 days after planting the plots are examined and the number of plants emerged and/or growing in each plot are counted. At 72 days after planting the percent bloom showing on plants in treated plots is determined. Data obtained are reported in Table IX below.

TABLE IX

Grain Sorghum Phytotoxicity Field Trials

| | | | University A | | University B | University C | |
|---|---|---|---|---|---|---|---|
| Treatment | Kg/ha | Placement | 14 DAT # Pl/ha | 38 DAT # Pl/ha | 16 DAT # Pl/ha | 21 DAT # Pl/ha | 72 DAT % Bloom |
| Terbufos 15 G | 2.24 | Inf | — | — | — | 9023 | 71.7 |
| Terbufos 15 PVCG | 2.24 | Inf | — | — | — | 12120 | 90.9 |
| Terbufos 15 G | 1.12 | Inf | 23303 | 22650 | 12466 | — | — |
| Terbufos 20 PVCG | 1.12 | Inf | 26927 | 20532 | 19066 | — | — |
| Terbufos 15 G | 2.24 | Inf | 20207 | 17925 | 14960 | — | — |
| Terbufos 20 PVCG | 2.24 | Inf | 27051 | 20206 | 16133 | — | — |
| Untreated Control | — | — | 28517 | 26073 | 32852 | 12254 | 81.7 |

Pl/ha = number of plants per hectare

EXAMPLE 10

Evaluation terbufos PVC granular compositions for corn rootworm control

The standard terbufos 15G ²⁴/₄₈ mesh product contains more particles per pound $4.7 \times 10^6$ than the 20% PVC granular composition of the invention i.e. $0.92 \times 10^6$. On this basis, the terbufos 15G product would be expected to have better distribution on application and, therefore, a greater probability of better biological efficacy than the 20% PVC granular product. Surprisingly, however, the 20% terbufos PVC granular product out performs the standard terbufos 15G product in field trials. In addition, the phorate 20% PVC granular product provides better corn rootworm control than the standard phorate 20% granular product.

The root rating system used to evaluate test compositions are as follows:

Root Rating System
1. No feeding
2. Visible Feeding Scars
3. At least 3 roots chewed to within ½ inch of the plant
4. One entire node of roots destroyed
5. Two nodes destroyed
6. Three or more nodes destroyed.

Corn rootworm control is determined in these tests. Row treatments with terbufos 15G standard granules, phorate 20G standard granules or phorate 25% PVC granules, are applied through a seven-inch bander mounted on the planter ahead of the press wheel. Furrow treatments are applied by removing the bander and allowing the granules to flow from the delivery tube directly into the seed furrow.

Two rows, 15 meters in length; are used for each treatment, and each treatment is replicated 2 to 4 times. The results of the tests are averaged and reported below.

| Field Studies For Corn Rootworm Efficacy | | |
|---|---|---|
| TREATMENT | N | ROOT RATING |
| Terbufos 15 G | 21 | 2.12 |
| Terbufos 20 PVCG | 21 | 2.02 |

*BANDED 1.12 kg/ha
N = number of tests
15 G = 15% granular (standard product)
20 PVCG = 20% Polyvinyl chloride granular
PR is probability

| Field Studies For Corn Rootworm Efficacy | | |
|---|---|---|
| HEAVY CORN ROOTWORM PRESSURE; CHECK > 4.5 | | |
| TREATMENT | N | ROOT RATING |
| Terbufos 15 G | 8 | 2.28 |
| Terbufos 20 PVCG | 8 | 2.07 |

*BANDED 1.12 kg/ha

-continued

Field Studies For Corn Rootworm Efficacy

| CORN ROOTWORM FIELD EFFICACY DATA | | |
|---|---|---|
| TREATMENT | BND | INF |
| Phorate 20 G | 2.64 | — |
| Phorate 25 PVCG | 2.58 | 2.31 (5) |
| CHECK | | 4.54 |

*7 LOCATIONS SIDE BY SIDE COMPARISONS
1.12 Kg/ha banded or in-furrow
20 G = 20% granular (standard product)
25 PVCG = 25% polyvinyl chloride granular product
BND = banded
Inf = in-furrow In these tests, the lower the root rating the more effective the protection afforded the root system by the treatment applied.

EXAMPLE 11

Evaluation of test compositions for systemic activity of terbufos, aldicarb and carbofuran PVC granular resin compositions In these tests the conventional 15% granular compositions of terbufos, aldicarb and carbofuran are used as controls along with an untreated check. The 15% PVC granular compositions of the invention, containing the above-identified soil insecticides, are prepared by the procedures of example 7 and the compositions evaluated are as follows:

| | Extruded Compositions | | |
|---|---|---|---|
| Ingredients | A | B | C |
| Carbofuran | 15.0 | — | |
| Aldibcarb | — | 15.0 | |
| Terbufos (87% Real) | — | — | 17.2 |
| Epoxidized Soy Oil | 1.0 | 1.0 | 1.0 |
| Butyl Benzyl Phthalate | 16.0 | 16.0 | 3.5 |
| Ca/Zn Stearate | 0.9 | 0.9 | 1.0 |
| PVC 2073 | 23.0 | 23.0 | 17.2 |
| CaSO$_4$, Anhydrous | 44.1 | 44.1 | 59.6 |
| Mono Glycerol Stearate | — | — | 0.5 |
| | 100.0 | 100.0 | 100.0 |

The evaluation is conducted as follows:

Silt loam prairie soil is placed in pots 8 inches wide by 4 inches deep. The depth of the soil is approximately 3 inches. A furrow 6 inches long and 1 inch deep is made in the center of each pot. Four seeds of radish, *Raphanus sativus* L., var. Cherry Bell, are placed in each furrow at 2 inch intervals. The granular treatments are manually distributed directly over the seeds in the furrow. The furrow is closed. When the first two true leaves have attained a diameter of approximately 1 inch (11 days after planting) a radish plant in each of two pots per replicate are infested with 10 green peach aphids, *Myzus persicae* and covered with four inch clear plastic drinking cups with the bottoms removed and replaced with nylon screen. The mortality counts are made 24 hours after infestation.

The percent mortality after 24 hours of exposure to the leaves of treated radish plants is shown below:

The radish plants originally planted are removed from the treated furrow and new seeds are planted 7 weeks after treatment. This procedure is designed to avoid the effects of senescence on uptake of the systemic insecticide.

Aphid mortality counts are made on radish plants 67 days after the original planting and in furrow treatment with the test compositions. Data obtained are reported in Table X below where it can be seen that the PVC granular compositions of the invention in all evaluations, provided better systemic control of aphids on replanted radish plants than any of the conventional formulations.

TABLE X

Evaluation of test compositions for systemic activity of terbufos, aldicarb and carbofuran PVC granular resin compositions.

| Composition | kg/ha | % Mortality |
|---|---|---|
| Terbufos 15 G | 0.57 | 35.0 |
| Terbufos 15 PVCG | 0.57 | 40.0 |
| Terbufos 15 G | 1.13 | 63.2 |
| Terbufos 15 PVCG | 1.13 | 76.9 |
| Aldicarb 15 G | 0.55 | 43.6 |
| Aldicarb 15 PVCG | 0.55 | 48.7 |
| Aldicarb 15 G | 1.09 | 40.0 |
| Aldicarb 15 PVCG | 1.09 | 75.8 |
| Carbofuran 15 G | 1.70 | 24.3 |
| Carbofuran 15 PVCG | 1.70 | 43.6 |
| Carbofuran 15 G | 3.40 | 36.6 |
| Carbofuran 15 PVCG | 3.40 | 44.7 |

EXAMPLE 12

Evaluation of chemical stability of the pesticide in conventional granular pesticide formulation and in PVC resin compositions of the invention In this evaluation stability of terbufos is determined in side by side stress tests of a 15% PVC granular composition prepared as described for formula A in Example 9 and a standard 15G product from a commercial run comprising 18.0% terbufos (86% real), 4.0% propylene glycol deactivator and 78% 24/48 mesh montmorillonite clay granules.

Samples from each of the terbufos 15G (24/48 mesh), standard product and the 15G PVC granular (24/48 mesh) product are stored for 3 months at 37° C. and 75% relative humidity. The products are assayed at the start and finish of the test period. Data obtained are reported below.

| | Terbufos Assay | | | |
|---|---|---|---|---|
| Formulation | Day 1 | | Day 90 | |
| Terbufos 15 G 24/48 mesh | 15.28 | 15.47 | 14.73 | 14.34 |
| Standard Product | 14.83 | 15.15 | 14.46 | 14.27 |
| Terbufos 15 PVCG 24/48 mesh Resin Product | 14.65 | 14.50 | 14.47 | 14.50 |
| | 14.52 | 14.47 | 14.49 | 14.37 |

From these data it can be seen that the standard 15G terbufos formulation assays 95.2% terbufos when stored for 3 months at 37° C. and 75% relative humidity; whereas, the PVC granular product of the invention assays 99.5% terbufos after storage for 3 months at 37° C. and 75% relative humidity.

From the above data it can be seen that the standard terbufos product containing deactivator looses a significant amount of activity on 90 days storage; whereas, the PVCG terbufos product of the invention, which contains no deactivator, is essentially stable over the same periods and shows little or no loss of product.

What is claimed is:

1. A pesticidal composition comprising: about 1.0% to 65.0%, by weight, of a pesticide, the technical grade of said pesticide having an oral and/or dermal LD50, as measured on rats or rabbits, of less than 50 mg/kg; about 5.0% to 60.0%, by weight, of a polyvinylic suspension resin having a weight average molecular weight of about 41,000 to 130,000; about 0.2% to 2.0% by weight, of a heat stabilizing agent or mixture of heat stabilizing agents for the resin; about 0.0% to 1.0%, by weight, of a lubricant; about 0.0% to 50.0%, by weight, of a secondary plasticizing agent; about 20% to 80.0%, by weight, of a mineral additive; and about 0.0% to 10.0% of silicon dioxide; wherein said pesticidal composition is a solid and has pesticide stability.

2. A pesticidal composition according to claim 1, wherein said resin is polyvinyl chloride suspension (PVC).

3. A pesticidal composition according to claim 2, wherein said pesticide is terbufos, phorate, fonofos, phosfolan, aldicarb, demeton, ethoprophos, thionazin, carbofuran, isofenphos, disulfoton or fensulfothion.

4. A pesticidal composition according to claim 3, wherein said pesticide is O,O-diethyl S-[[(1,1-dimethylethyl)thio]methyl]phosphorodithioate.

5. A pesticidal composition according to claim 3, wherein said pesticide is O,O-diethyl s-(ethylthiomethyl) phosphorodithioate.

6. A pesticidal composition according to claim 1 comprising: about 4.0% to 65.0%, by weight, of said pesticide; about 5.0% to 60.0%, by weight, of said polyvinylic resin; about 0.2% to 1.0%, by weight, of said heat stabilizing agent or mixture thereof; and about 0.0% to 2.0%, by weight, of said lubricant.

7. A pesticidal composition according to claim 1 comprising: about 1.0% to 30.0%, by weight, of said pesticide; about 5.0% to 60.0%, by weight, of said polyvinylic resin; about 0.2% to 2.0%, by weight, of said heat stabilizing agent or mixture of heat stabilizing agents; about 0% to 2.0%, by weight, of said lubricant; about 0.0% to 50.0%, by weight, of said secondary plasticizing agent; about 20.0% to about 80.0%, by weight, of said mineral additive; and 0.0% to 2.0%, by weight, of $SiO_2$.

8. A pesticidal composition according to claim 7, wherein said resin is polyvinyl chloride suspension (PVC).

9. A pesticidal composition according to claim 8, wherein said pesticide is terbufos, phorate, fonofos, phosfolan, aldicarb, demeton, ethoprophos, thionazin, carbofuran, isofenphos, disulfoton or fensulfothion.

10. A pesticidal composition according to claim 9, wherein said pesticide is O,O-diethyl S-[[(1,1-dimethylethyl)thio]methyl]phosphorodithioate and wherein said PVC resin has a weight average molecular weight of about 50,000 to 69,000.

11. A pesticidal composition according to claim 10, wherein said pesticide is O,O-diethyl-S-(ethylthiomethyl) phosphorodithioate and wherein said PVC resin has a weight average molecular weight of about 50,000 to 69,000.

12. A pesticidal composition according to claim 7, wherein said polyvinylic resin is polyvinyl chloride suspension resin, polyvinyl acetate or polyvinyl alcohol; said secondary plasticizer is organic phthalate, organic phosphate, organic adipate, epoxidized tall oil, epoxidized vegetable oil, organic trimellitate or organic citrate; said stabilizing agent is metal stearate, alkaline earth metal stearate, epoxidized vegetable oil, organic tin complex or organic phosphite; said lubricant is alkaline earth metal stearate, stearic acid, paraffin wax, amide wax, magnesium, lead or aluminum stearate or a low molecular weight polyethylene; and said mineral additive is alkaline earth metal sulfate or carbonate, clay, mica, wallstonite or cellulose product.

13. A pesticidal composition according to claim 1, wherein said pesticidal composition has extended biological activity.

14. A pesticidal resin composition comprising:

about 1.0% to 30.0%, by weight, of a pesticide, the technical grade of said pesticide having an oral and/or dermal LD50, measured on rats or rabbits, of less than 50 mg/kg; about 5.0% to 60.0%, by weight, of a polyvinyl chloride resin having a weight average molecular weight of about 50,000 to 69,000; about 0.2% to 25.0%, by weight, of a secondary plasticizing agent; about 20.0% to 55.0%, by weight, of a mineral additive; about 0.0% to 2.0% of a lubricant; and about 0.0% to 10.0%, by weight, of $SiO_2$; wherein said pesticidal composition is pelletized and has a reduced mammalian toxicity.

15. A pesticidal resin composition according to claim 14, wherein said pesticide is O,O-diethyl s-[[(1,1-dimethylethyl)thio]methyl]phosphorodithioate or O,O-diethyl-S-(ethylthiomethyl)phosphorodithioate.

16. A pesticidal resin composition according to claim 15, wherein said resin stabilizing agent is metal stearate, alkaline earth metal stearate, calcium/zinc stearate, epoxidized soybean oil or mixtures thereof; said secondary plasticizing agent is butyl benzyl phthalate, tricresyl phosphate, soybean oil, trioctyl mellitate, diisononyl phthalate, organic citrates, acetyl tributylcitrate or mixtures thereof; and said mineral additive is alkaline earth metal sulfates, alkaline earth metal carbonates, clay, mica, wallstonite, cellulose products, or mixtures thereof.

* * * * *